United States Patent

Isoda et al.

Patent Number: 5,831,110
Date of Patent: Nov. 3, 1998

[54] FLUORINE-CONTAINING SILOXANE COMPOUND AND PROCESS FOR PRODUCTION THEREOF

[75] Inventors: Yuichi Isoda; Koichi Ayama, both of Kumamoto, Japan

[73] Assignee: Chisso Corporation, Osaki, Japan

[21] Appl. No.: 42,737

[22] Filed: Mar. 17, 1998

[30] Foreign Application Priority Data

Oct. 23, 1997 [JP] Japan ................................. 9-309204
Nov. 21, 1997 [JP] Japan ................................. 9-337819

[51] Int. Cl.⁶ .................................................. C07F 7/10
[52] U.S. Cl. .................................................. 556/414
[58] Field of Search ........................................ 556/414

[56] References Cited

FOREIGN PATENT DOCUMENTS

| | | |
|---|---|---|
| 2-115190 | 4/1990 | Japan . |
| 3-251589 | 11/1991 | Japan . |
| 6-792 | 1/1994 | Japan . |
| 7-793 | 1/1995 | Japan . |
| 8-157483 | 6/1996 | Japan . |

*Primary Examiner*—Paul F. Shaver
*Attorney, Agent, or Firm*—Oblon, Spivak, McClelland, Maier & Neustadt, P.C.

[57] ABSTRACT

According to the present invention there is disclosed a process for producing a fluorine-containing siloxane compound represented by the formula (3):

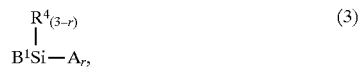

[wherein A is a fluorine-containing organic group represented by the formula (4):

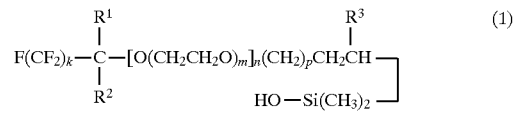

(wherein $R^1$ and $R^2$ are each independently a fluorine atom or a trifluoromethyl group, $R^3$ is a hydrogen atom or a straight chain or branched chain hydrocarbon group having 1 to 8 carbon atoms, k is an integer of 0 to 16, m is an integer of 0 to 30, n is 0 or 1, and p is an integer of 0 to 9); r is an integer of 1 to 3; $R^4$ is a monovalent hydrocarbon group having 1 to 6 carbon atoms; and $B^1$ is a hydrogen atom, a methacryloxypropyl group or a vinyl group], which process comprises reacting a fluorine-containing silane represented by the formula (1):

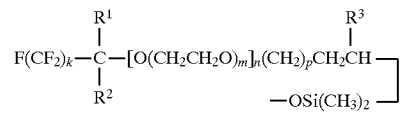

(wherein $R^1$, $R^2$, $R^3$, k, m, n and p have the same definitions as given above) with a chlorosilane represented by the formula (2):

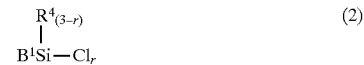

(wherein $R^4$, $B^1$ and r have the same definitions as given above). There is also disclosed a fluorine-containing siloxane compound of the formula (3) wherein $B^1$ is an isocyanate-containing group.

5 Claims, 5 Drawing Sheets

FLUORINE-CONTAINING SILOXANE COMPOUND AND PROCESS FOR PRODUCTION THEREOF

BACKGROUND OF THE INVENTION

1. Field of the Invention

The present invention relates to a process for producing a fluorine-containing organosilicon compound. More particularly, the present invention relates to a process for producing a siloxane compound having, in the molecule, a fluorine-containing organic group and a reactive silyl group; and a siloxane having, in the molecule, a fluorine-containing organic group and an isocyanate group, which is effective for uses such as chemical modification of organic compound and the like, and a process for production thereof.

2. Description of the Related Arts

It has been conducted to introduce, into an organic compound, a fluorine-containing organic group using a reactive fluorine-containing organic compound having said fluorine-containing organic group, to allow the former organic-compound to have improved properties in water repellency, oil repellency, releasability, chemical resistance, etc. The fluorine-containing organic compound has a highly reactive functional group so that the fluorine-containing organic group of the compound can be introduced into the former organic compound. Therefore, the fluorine-containing organic compound is inferior in heat resistance and hydrolysis resistance.

In order to solve the above problem, it was attempted to allow a silicone compound to be present between the fluorine-containing organic group and reactive functional group of the fluorine-containing organic compound.

For example, in (a) Japanese Patent Application Laid-Open No. 115190/1990, there is disclosed a process for producing a reactive fluorine-containing organic compound having a disiloxane group, which process comprises subjecting 1,1,3,3-tetramethyl-1,3-disiloxane and a disiloxane having a perfluoro group as a substituent, to an equilibration reaction in the presence of an acid reaction. Also, for example, in (b) Japanese Patent Publication No. 792/1994, there is disclosed a process which comprises reacting 1,1,3,3-tetramethyl-1,3-disiloxane with a chlorosilane having a fluorine-containing group, in the presence of concentrated hydrochloric acid.

With the process described in (a), however, the disiloxane used as a raw material remains in the reaction product, or disiloxanes other than the intended product are formed as by-products in large amounts; therefore, it is difficult to selectively obtain the intended product alone. With the process described in (b), it is necessary to use 1,1,3,3-tetramethyl-1,3-disiloxane in excess relative to the chlorosilane having a fluorine-containing group and further to use concentrated hydrochloric acid in a large amount; therefore, further improvements are required in production cost and production facility.

Also in (c) Japanese Patent Application Laid-Open No. 251589/1991 is disclosed a compound wherein a fluorine-containing organic group and an alkyl group are bonded by a siloxane linkage; in (d) Japanese Patent Application Laid-Open No. 793/1995 is disclosed a compound having a fluorine-containing organic group and an oxyalkylene group via a siloxane linkage; and in (e) Japanese Patent Application Laid-Open No. 157483/1996 is disclosed a chlorosilane or alkoxysilane compound having a fluorine-containing organic group.

The compounds disclosed in (c) and (d) are additives or surfactants to be added to an organic substance such as polymer or the like. However, the compound wherein a fluorine-containing organic group and an alkyl group are bonded by a siloxane linkage, is not chemically bonded with the organic substance. As a result, in some cases, the compound added to the organic substance may bleed out from the organic substance-compound mixture with the lapse of time, and the addition effect of the compound may not last long.

The compound disclosed in (e) has a highly reactive alkoxysilyl or chlorosilyl group as a functional group. Therefore, the compound is useful when used for chemical modification of the surface of a powder or a metal, whose surface is reactive with the functional group. When the compound is used for chemical modification of an organic compound such as organic resin or the like, however, the alkoxysilyl or chlorosilyl group of the fluorine-containing siloxane compound reacts with the organic resin to form a carbon-oxygen-silicon linkage having high hydrolyzability. Therefore, the organic compound (e.g. organic resin) which has been subjected to chemical modification with the above compound, undergoes hydrolysis at the above linkage site during the use and liberates a fluorine-containing siloxane compound. Thus, the effect of modification does not last long.

Hence, in chemical modification of an organic compound with a fluorine-containing organic compound, it is desired to bond the organic compound and the fluorine-containing organic group of the latter compound with a strong chemical linkage in order to allow the modification effect to last semipermanently.

SUMMARY OF THE INVENTION

The present invention has been completed with an aim of providing a fluorine-containing siloxane compound capable of solving the above-mentioned problem and a process for producing the compound at a high yield at a low cost.

The first invention is as follows.

A process for producing a fluorine-containing siloxane compound represented by the formula (3):

[wherein A is a fluorine-containing organic group represented by the formula (4):

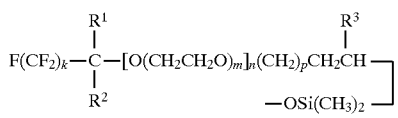

(wherein $R^1$ and $R^2$ are each independently a fluorine atom or a trifluoromethyl group, $R^3$ is a hydrogen atom or a straight chain or branched chain hydrocarbon group having 1 to 8 carbon atoms, k is an integer of 0 to 16, m is an integer of 0 to 30, n is 0 or 1, and p is an integer of 0 to 9); r is an integer of 1 to 3; $R^4$ is a monovalent hydrocarbon group having 1 to 6 carbon atoms; and $B^1$ is a hydrogen atom, a methacryloxypropyl group or a vinyl group], which process comprises reacting a fluorine-containing silane represented by the formula (1):

$$\text{F(CF}_2)_k-\underset{\underset{R^2}{|}}{\overset{\overset{R^1}{|}}{C}}-[O(CH_2CH_2O)_m]_n(CH_2)_pCH_2\underset{\underset{HO-Si(CH_3)_2}{|}}{CH}- \quad (1)$$

(wherein $R^1$, $R^2$, $R^3$, k, m, n and p have the same definitions as given above) with a chlorosilane represented by the formula (2):

$$\underset{\underset{B^1Si-Cl_r}{|}}{R^4{}_{(3-r)}} \quad (2)$$

(wherein $R^4$, $B^1$ and r have the same definitions as given above).

The second invention is as follows.

A fluorine-containing siloxane compound represented by the formula (6):

$$\underset{\underset{B^2Si-A_r}{|}}{R^4{}_{(3-r)}} \quad (6)$$

wherein A is a fluorine-containing organic group represented by the formula (7):

$$\text{F(CF}_2)_k-\underset{\underset{R^2}{|}}{\overset{\overset{R^1}{|}}{C}}-[O(CH_2CH_2O)_m]_n(CH_2)_pCH_2CH- \atop {-(OSi)_q-\atop \underset{Me}{|}}^{\overset{Me}{|}} \quad (7)$$

(wherein $R^1$ and $R^2$ are each independently a fluorine atom or a trifluoromethyl group, $R^3$ is a hydrogen atom or a straight chain or branched chain hydrocarbon group having 1 to 8 carbon atoms, Me is a methyl group, k is an integer of 0 to 16, m is an integer of 0 to 30, n is 0 or 1, p is an integer of 0 to 9, and q is an integer of 1 to 1,000); r is an integer of 1 to 3; $R^4$ is a monovalent hydrocarbon group having 1 to 6 carbon atoms; and $B^2$ is an isocyanate-containing group represented by the formula (8):

$$-CH_2CH-\underset{}{\overset{CH_3}{|}}\underset{}{\bigcirc}\underset{CH_3}{\overset{CH_3}{\underset{|}{\overset{|}{C}}-N=C=O}} \quad (8)$$

A process for producing a fluorine-containing siloxane compound represented by the formula (6):

$$\underset{\underset{B^2Si-A_r}{|}}{R^4{}_{(3-r)}} \quad (6)$$

[wherein A is a fluorine-containing organic group represented by the formula (7):

$$\text{F(CF}_2)_k-\underset{\underset{R^2}{|}}{\overset{\overset{R^1}{|}}{C}}-[O(CH_2CH_2O)_m]_n(CH_2)_pCH_2CH- \atop {-(OSi)_q-\atop \underset{Me}{|}}^{\overset{Me}{|}} \quad (7)$$

(wherein $R^1$ and $R^2$ are each independently a fluorine atom or a trifluoromethyl group, $R^3$ is a hydrogen atom or a straight chain or branched chain hydrocarbon group having 1 to 8 carbon atoms, Me is a methyl group, k is an integer of 0 to 16, m is an integer of 0 to 30, n is 0 or 1, p is an integer of 0 to 9, and q is an integer of 1 to 1,000); r is an integer of 1 to 3; $B^2$ is an isocyanate-containing group represented by the formula (8):

$$-CH_2CH-\underset{}{\overset{CH_3}{|}}\underset{}{\bigcirc}\underset{CH_3}{\overset{CH_3}{\underset{|}{\overset{|}{C}}-N=C=O}} \quad (8)$$

and $R^4$ is a monovalent hydrocarbon group having 1 to 6 carbon atoms], which process comprises reacting a hydrosilyl group-containing siloxane compound represented by the formula (9):

$$\underset{\underset{HSi-A_r}{|}}{R^4{}_{(3-r)}} \quad (9)$$

(wherein A, r and $R^4$ have the same definitions as given above) with an unsaturated group-containing isocyanate compound represented by the formula (10):

$$CH_2=\underset{\underset{}{\overset{CH_3}{|}}}{C}-\underset{}{\bigcirc}-\underset{CH_3}{\overset{CH_3}{\underset{|}{\overset{|}{C}}-N=C=O}} \quad (10)$$

in the presence of a platinum-containing compound as a catalyst.

According to the process of the first invention, a fluorine-containing siloxane compound can be produced in a large amount with a low-cost facility, without using an expensive hydrosilyl group-containing silicon compound in excess or without using any corrosive raw material. Moreover, since the process gives a high yield, the fluorine-containing siloxane compound can be produced at a low cost.

The isocyanate group-containing siloxane compound according to the second invention has, in the molecule, a highly reactive isocyanate group and a fluorine-containing organic group having excellent water- and oil-repellency, releasability and chemical resistance, and can therefore be used for improvement of properties, etc. of various organic compounds. The siloxane compound of the second invention forms a stable chemical linkage particularly when reacted with an organic compound having a functional group highly reactive with the isocyanate group of the siloxane compound, such as hydroxyl group, amino group, amide group, carboxyl group or the like, whereby the siloxane compound can improve the properties, etc. of such an organic compound. Moreover, the effect of the property improvement lasts semipermanently.

DETAILED DESCRIPTION OF THE PREFERRED EMBODIMENTS

The First Invention

Figure 1:
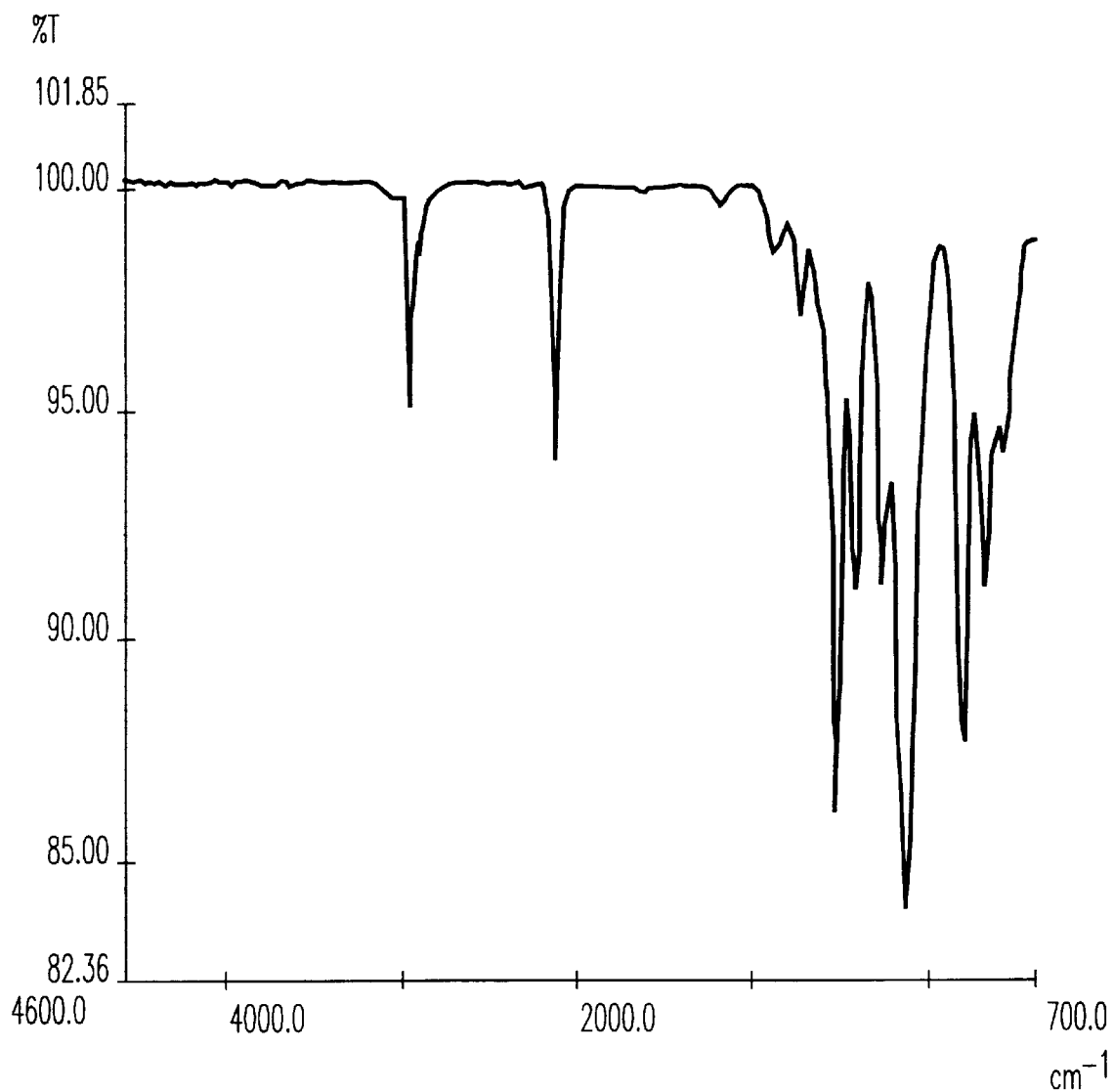
FIG. 1 is a GC-IR chart of the disiloxane compound obtained in Example 1.

The first invention is a process for producing a fluorine-containing siloxane compound represented by the following formula (3) at a low cost and at a high yield by reacting a fluorine-containing silane represented by the following formula (1) with a chlorosilane represented by the following formula (2).

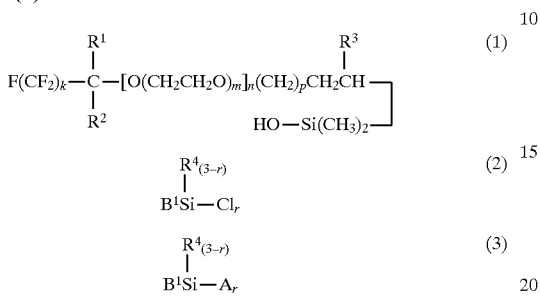

In the above formulas (1) to (3), $R^1$ and $R^2$ are each independently a fluorine atom or a trifluoromethyl group; $R^3$ is a hydrogen atom or a straight chain or branched chain hydrocarbon group having 1 to 8 carbon atoms; k is an integer of 0 to 16; m is an integer of 0 to 30; n is 0 or 1; p is an integer of 0 to 9; $R^4$ is a monovalent hydrocarbon group having 1 to 6 carbon atoms; r is an integer of 1 to 3; $B^1$ is a hydrogen atom, a methacryloxypropyl group or a vinyl group; and A is a fluorine-containing organic group represented by the following formula (4):

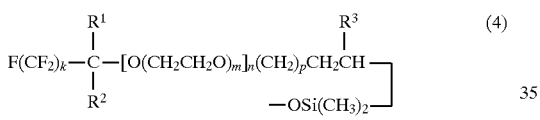

(wherein $R^1$, $R^2$, $R^3$, k, m, n and p have the same definitions as given above).

The fluorine-containing silane represented by the formula (1), used in the present invention is preferably a compound obtained by hydrolyzing a fluorine-containing chlorosilane represented by the following formula (5):

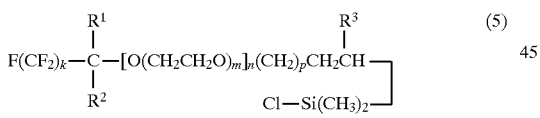

wherein $R^1$, $R^2$, $R^3$, k, m, n and p have the same definitions as given above.

Specific examples of the fluorine-containing chlorosilane (5) include the following compounds.

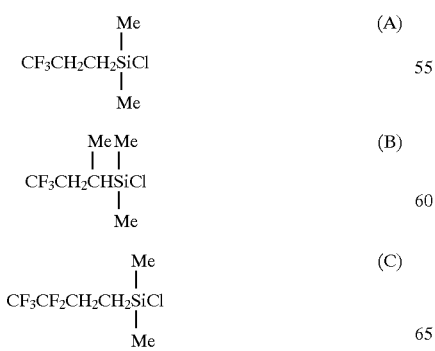

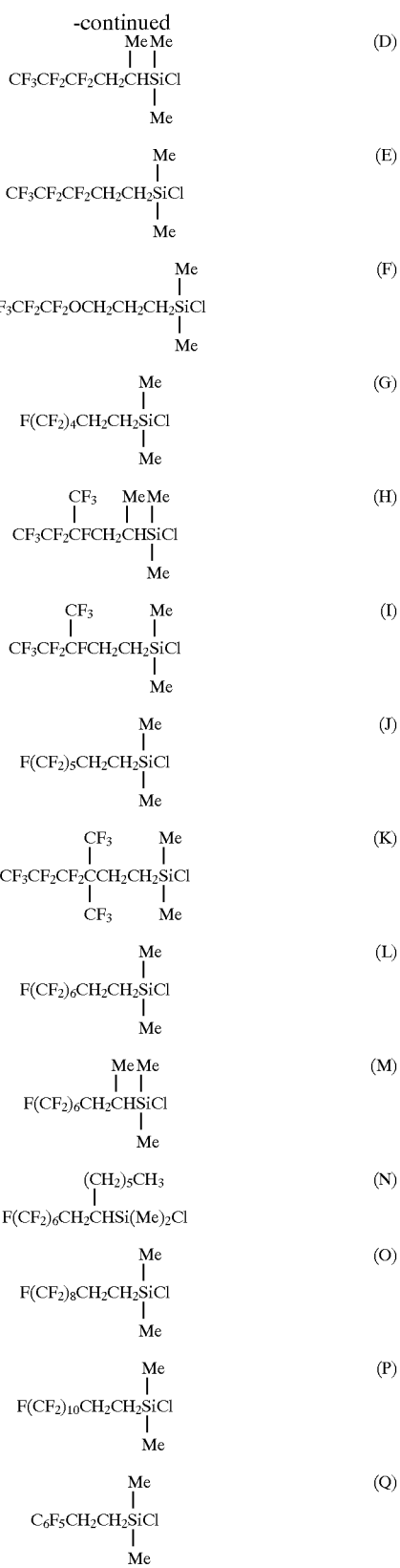

The chlorosilane used in the present invention is represented by the formula (2). In the formula (2), r is an integer of 1 to 3; $B^1$ is a hydrogen atom, a methacryloxypropyl group or a vinyl group; and $R^4$ is a monovalent hydrocarbon group having 1 to 6 carbon atoms. Specific examples of $R^4$ are straight chain or branched chain alkyl groups such as methyl, ethyl, propyl, butyl, hexyl and the like; a cyclohexyl group; alkenyl groups such as vinyl, allyl and the like; and a phenyl group.

Specific examples of the chlorosilane represented by the formula (2) are trichlorosilane, methyldichlorosilane, dimethylchlorosilane, methacryloxypropyldimethylchlorosilane, methacryloxypropylmethyldichlorosilane and vinyldimethylchlorosilane.

In the reaction of the fluorine-containing silane represented by the formula (1) with the chlorosilane represented by the formula (2), a solvent may be or may not be used. When a solvent is used, the solvent is preferably inert to the chlorosilane. Use of a solvent (e.g. an alcohol) having an active hydrogen group reactive with the chlorosilane is not preferable.

Examples of an preferable solvent are toluene, hexane and ether, all of which are commonly used as a solvent.

With respect to the reaction temperature, no heating is necessary because the reaction is rapid; however, heating may be applied as necessary. Since the reaction is exothermic, care must be taken in heating so that heat generation does not incur too high a temperature which is higher than the boiling point(s) of the raw material (s) used. The reaction is not disturbed even if the reaction temperature exceeds the boiling point(s), but such a high reaction temperature is not preferable for safety. The reaction temperature is particularly preferably $-10°$ to $60°$ C.

In the reaction, hydrochloric acid is formed which is derived from the chlorine atom(s) of the chlorosilane used as a raw material. Therefore, it is preferable to add, into the reaction system, a base for neutralization of the hydrochloric acid. The base is particularly preferably a tertiary amine such as triethylamine or the like. Any base other than the tertiary amine can be used as long as it does not disturb the reaction of the first invention. The base is used in an amount of preferably at least one mole per mole of the chlorine of the chlorosilane. The amount of the base is preferably about 1 to 1.5 moles relative to the chlorine, for neutralization of the HCl generated and need not be a large excess.

In the reaction of the fluorine-containing silane of the formula (1) with the chlorosilane of the formula (2), the two compounds are preferably reacted so that the molar ratio of the silanol group in the former compound and the chlorine in the latter compound becomes 1:1. A molar ratio deviating from the above ratio does not disturb the reaction. However, since use of either compound in excess produces no merit, the above molar ratio of 1:1 is preferred for a cost reason.

By conducting the reaction of the first invention using the fluorine-containing silane of the formula (1) [obtained by hydrolysis of one of the above-mentioned fluorine-containing chlorosilanes (A) to (Q)] and the chlorosilane of the formula (2), a corresponding fluorine-containing siloxane compound can be produced.

The Second Invention

As mentioned previously, the fluorine-containing siloxane compound of the second invention is represented by the following formula (6):

The fluorine-containing siloxane compound represented by the formula (6) can be produced by reacting a hydrosilyl group-containing siloxane compound represented by the following formula (9):

with an isocyanate compound having an unsaturated group, represented by the following formula (10), in the presence of a platinum-containing compound as a catalyst:

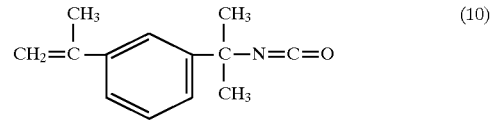

In the formulas (6), (9) and (10), $R^4$ is a monovalent hydrocarbon group having 1 to 6 carbon atoms; r is an integer of 1 to 3; $B^2$ is an isocyanate-containing group represented by the following formula (8):

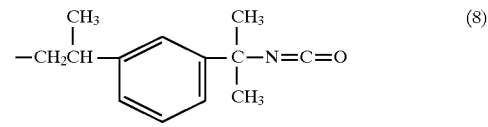

and A is a fluorine-containing organic group represented by the following formula (7):

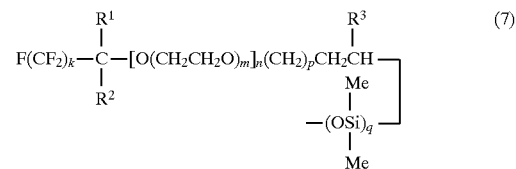

wherein $R^1$ and $R^2$ are each independently a fluorine atom or a trifluoromethyl group, $R^3$ is a hydrogen atom or a straight chain or branched chain hydrocarbon group having 1 to 8 carbon atoms, Me is a methyl group, k is an integer of 0 to 16, m is an integer of 0 to 30, n is 0 or 1, p is an integer of 0 to 9, and q is an integer of 1 to 1,000.

The reaction of the hydrosilyl group-containing siloxane compound (9) with the unsaturated group-containing isocyanate compound (10) is a hydrosilylation reaction.

In the reaction, the proportions of the hydrosilyl group-containing siloxane compound (9) and the unsaturated group-containing isocyanate compound (10) is preferably 1:1 to 1:2 in terms of molar ratio.

When the proportion of the unsaturated group-containing isocyanate compound (10) is less than one mole per mole of the hydrosilyl group-containing siloxane compound (9), part of the hydrosilyl group-containing siloxane compound (9) remains unreacted in the reaction mixture. Therefore, the proportion of the unsaturated group-containing isocyanate compound (10) is preferably at least equimolar with the hydrosilyl group-containing siloxane compound (9). Use of the unsaturated group-containing isocyanate compound (10) in an amount more than necessary, however, produces no merit and rather requires an additional step for removing the unsaturated group-containing isocyanate compound (10) remaining in the reaction mixture, resulting in a higher production cost. Therefore, the proportions of the hydrosilyl group-containing siloxane compound (9) and the unsaturated group-containing isocyanate compound (10) are preferred to be in the above range.

In the hydrosilylation reaction, a solvent may be or may not be used. When a solvent is used, it may be any solvent which does not impair the catalytic activity of the platinum-based catalyst used in the reaction or does not react with Si—H linkage. The solvent can be exemplified by aromatic hydrocarbons (e.g. toluene and xylene), saturated aliphatic hydrocarbons (e.g. pentane, hexane and heptane) and ethers (e.g. tetrahydrofuran and diethyl ether), all being ordinary solvents.

The platinum-containing compound used as the catalyst in the hydrosilylation reaction can be a platinum-containing compound commonly used as a catalyst in a hydrosilylation reaction. Specific examples of the catalyst are preferably chloroplatinic acid, alcohol-modified chloroplatinic acid, platinum complex of divinyltetramethyldisiloxane, platinum complex of cyclovinylmethylsiloxane, platinum carbonyl complex and platinum pyridine complex; particularly preferably platinum complex of divinyltetramethyldisiloxane and platinum complex of cyclovinylmethylsiloxane.

The reaction temperature is preferably room temperature to 150° C. When a starting material with low-boiling is used, a high reaction temperature may evaporate the starting material. Too low reaction temperature may require a long time for completion of the reaction. Therefore, the reaction temperature is particularly preferably 40° to 100° C.

The reaction time depends upon the reaction temperature used, etc. but is preferred to be generally 3 to 24 hours.

The hydrosilyl group-containing siloxane compound (9) used in the hydrosilylation reaction can be obtained by reacting a fluorine-containing silane represented by the following formula (11) with a chlorosilane represented by the following formula (12).

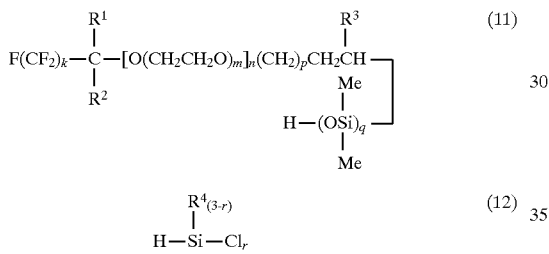

In the above formulas (11) and (12), $R^1$, $R^2$, $R^3$, Me, k, m, n, p, q, $R^4$ and r have the same definitions as give above.

Specific examples of the chlorosilane (12) are trichlorosilane, methyldichlorosilane, dimethylchlorosilane and those chlorosilanes of the formula (12) wherein $R^4$ is a straight chain or branched chain alkyl group (e.g. methyl, ethyl, propyl, butyl or hexyl), a cyclohexyl group, a phenyl group, a phenethyl group or the like.

The hydrosilyl group-containing siloxane compound (9) can also be produced by polymerizing a cyclic monomer represented by the following formula (13) using, as an initiator, a fluorine-containing lithium silanolate represented by the following formula (14), and terminating the polymerization with the above-mentioned chlorosilane (12).

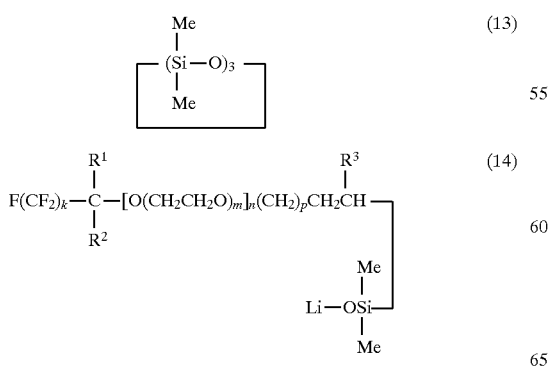

In the formulas (13) and (14), Me, $R^1$, $R^2$, $R^3$, k, m, n and p have the same definitions as give above.

Other processes for producing the hydrosilyl group-containing siloxane compound (9) are disclosed in Japanese Patent Publication No. 792/1994, etc. Needless to say, the process for producing the hydrosilyl group-containing siloxane compound (9) used in the present invention is not restricted to the above-mentioned processes.

Specific examples of the hydrosilyl group-containing siloxane compound (9) used in the present invention are shown below but are not restricted thereto.

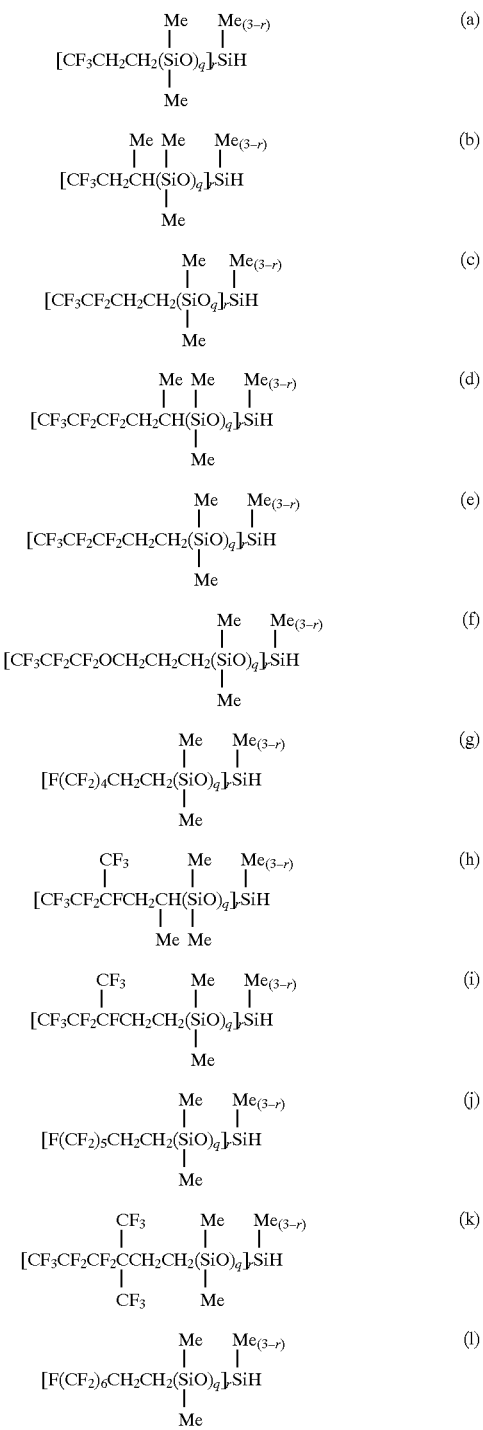

-continued $$[F(CF_2)_6CH_2CH(SiO)_q]_r SiH \text{ with Me, Me, Me}_{(3-r)}, \text{ Me substituents} \quad (m)$$

$$\begin{array}{c} (CH_2)_5CH_3 \\ | \\ [F(CF_2)_6CH_2CH(SiO)_q]_r SiH \text{ with Me, Me}_{(3-r)}, \text{ Me} \end{array} \quad (n)$$

$$[F(CF_2)_8CH_2CH_2(SiO)_q]_r SiH \text{ with Me, Me}_{(3-r)}, \text{ Me} \quad (o)$$

$$[F(CF_2)_{10}CH_2CH_2(SiO)_q]_r SiH \text{ with Me, Me}_{(3-r)}, \text{ Me} \quad (p)$$

By subjecting one of the above hydrosilyl group-containing siloxane compounds (a) to (p) and an unsaturated group-containing isocyanate compound (10) to a hydrosilylation reaction, a corresponding fluorine-containing siloxane compound (6) can be produced.

The present invention is specifically described below with reference to Examples.

EXAMPLES OF THE FIRST INVENTION

Example 1

Production Example of $$CF_3CH_2CH_2-\underset{\underset{CH_3}{|}}{\overset{\overset{CH_3}{|}}{Si}}-O-\underset{\underset{CH_3}{|}}{\overset{\overset{CH_3}{|}}{Si}}-H$$

(a) Production of Fluorine-containing Silane

Into a 500-ml three-necked flask were fed 39.7 g (0.39 mole) of triethylamine, 47.2 g (2.62 moles) of pure water and 77.4 g of tetrahydrofuran. The mixture was stirred by the use of a stirrer while the mixture was kept at 5° C. with ice water. Thereto was dropwise added 50.0 g (0.26 mole) of 3,3,3-trifluoropropyldimethylchlorosilane in 2 hours. After the completion of the dropwise addition, the mixture was stirred for 1 hour while the mixture was kept at 10° C. or lower. Acetic acid was added to make the mixture acidic. Then, extraction was conducted with 500 ml of hexane. The extract was washed with water and then dried on anhydrous magnesium sulfate.

(b) Production of Fluorine-containing Siloxane

To the dried extract obtained above was added 39.7 g (0.39 mole) of triethylamine, and the mixture was kept at 5° C. Thereto was dropwise added 24.6 g (0.26 mole) of dimethylchlorosilane in a nitrogen atomosphere in 2 hours. The mixture was stirred for 2 hours, followed by addition of dilute hydrochloric acid for neutralization.

The resulting reaction mixture was washed with water and then dried on anhydrous magnesium sulfate. The resulting compound solution was meausred for GC-MS and GC-IR spectrum.

The results are shown below.

Yield: 96% (GC analysis by internal standard method)

GC-MS: [M+1]=231

GC-IR: the spectrum chart is shown in FIG. 1.

From the above results, the substance obtained was confirmed to be a disiloxane compound represented by the following structural formula (15).

$$CF_3CH_2CH_2-\underset{\underset{CH_3}{|}}{\overset{\overset{CH_3}{|}}{Si}}-O-\underset{\underset{CH_3}{|}}{\overset{\overset{CH_3}{|}}{Si}}-H \quad (15)$$

Example 2

A fluorine-containing silane solution was obtained in the same manner as in Example 1 (a). Thereto was added 39.7 g (0.39 mole) of triethylamine. The mixture was cooled to 5° C. with ice water. Thereto was dropwise added 57.4 g (0.26 mole) of 3-methacryloxypropyldimethylchlorosilane in a nitrogen atmosphere in 2 hours. The mixture was stirred for 4 hours, followed by addition of dilute hydrochloric acid for neutralization. The resulting reaction mixture was washed with water and then dried on anhydrous magnesium sulfate. The dried mixture was measured for GC-MS and GC-IR spectrum. The results are shown below.

Yield: 95% (GC analysis by internal standard method)

Figure 2:
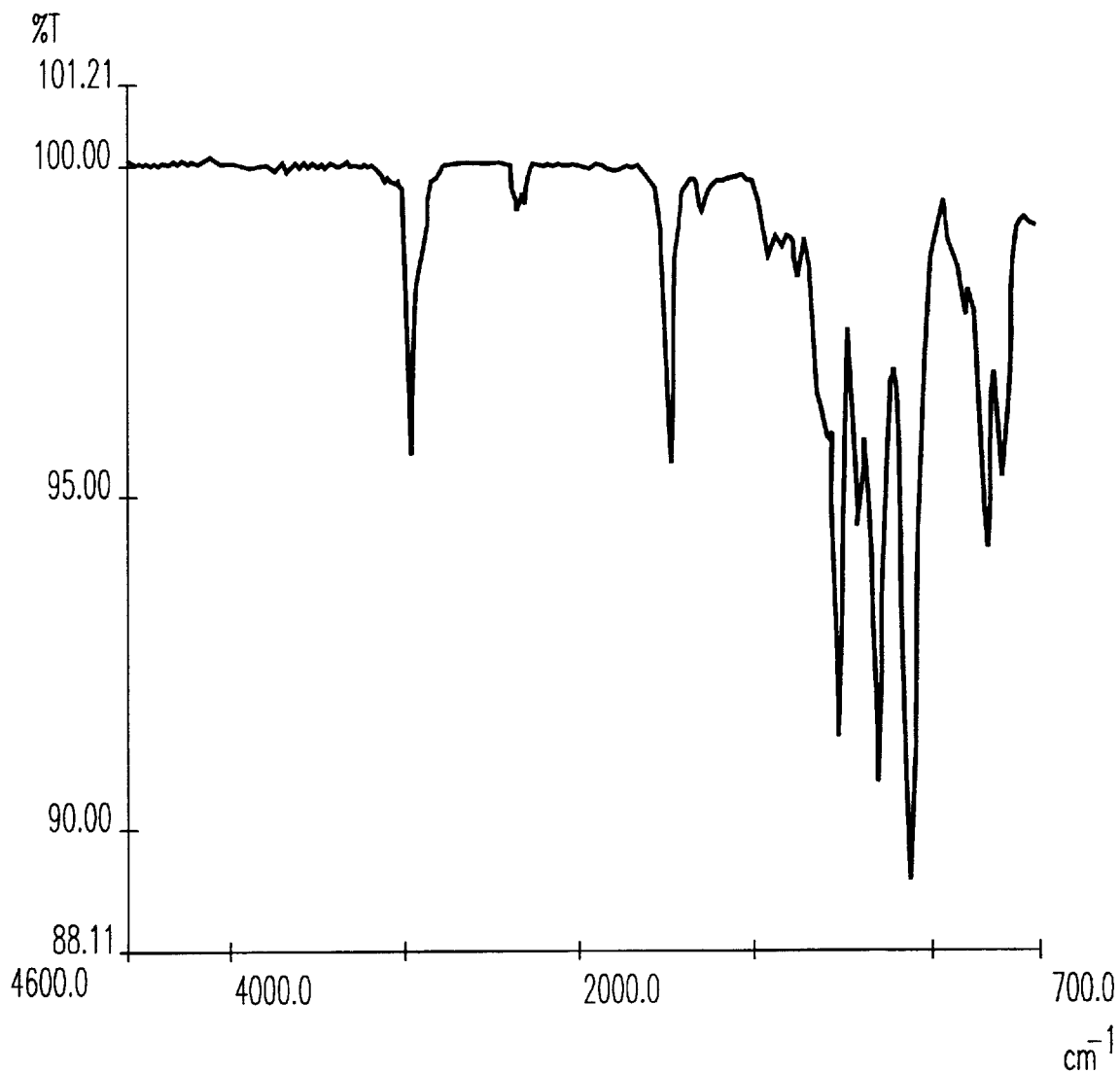
FIG. 2 is a GC-IR chart of the disiloxane compound obtained in Example 2.

GC-IR: the spectrum chart is shown in FIG. 2.

From the above results, the compound obtained was confirmed to be a disiloxane compound represented by the following structural formula (16).

$$CF_3CH_2CH_2\underset{\underset{CH_3}{|}}{\overset{\overset{CH_3}{|}}{Si}}-O-\underset{\underset{CH_3}{|}}{\overset{\overset{CH_3}{|}}{Si}}CH_2CH_2CH_2O\underset{\underset{O}{\|}}{\overset{\overset{CH_3}{|}}{C}}C=CH_2 \quad (16)$$

EXAMPLES OF THE SECOND INVENTION

Example 3

Production of Fluorine-containing Disiloxane

Into a 500-ml three-necked flask were fed 39.7 g (0.39 mole) of triethylamine, 47.2 g (2.62 moles) of pure water and 77.4 g of tetrahydrofuran. The mixture was stirred by the use of a stirrer while the mixture was kept at 50° C. with ice water. Thereto was dropwise added 50.0 g (0.26 mole) of 3,3,3-trifluoropropyldimethylchlorosilane in 2 hours. After the completion of the dropwise addition, the mixture was stirred for 1 hour while the mixture was kept at 10° C. or lower. Acetic acid was added to make the mixture acidic. Then, extraction was conducted with 500 ml of hexane. The extract was washed with water and then dried on anhydrous magnesium sulfate.

To the dried extract obtained above was added 39.7 g (0.39 mole) of triethylamine, and the mixture was kept at 5° C. with ice water. Thereto was dropwise added 24.6 g (0.26 mole) of dimethylchlorosilane in a nitrogen atmosphere in 2 hours. The mixture was stirred for 2 hours, followed by addition of dilute hydrochloric acid for neutralization.

The resulting reaction mixture was washed with water and then dried on anhydrous magnesium sulfate to obtain 1-(3,3,3-trifluoropropyl)-1,1,3,3-tetramethyldisiloxane represented by the following structural formula (17). Quantitative analysis by internal standard method indicated that the yield of the compound was 99%.

$$CF_3CH_2CH_2-\underset{\underset{CH_3}{|}}{\overset{\overset{CH_3}{|}}{Si}}-O-\underset{\underset{CH_3}{|}}{\overset{\overset{CH_3}{|}}{Si}}-H \quad (17)$$

Production of Isocyanate Group-containing Disiloxane

Into a 100-ml three-necked flask equipped with a cooler and a stirrer were fed 1/5 weight part of the above-obtained solution of 1-(3,3,3-trifluoropropyl)-1,1,3,3-tetramethyldisiloxane [which contained 12.0 g (0.051 mole) of the disiloxane], 11.5 g (0.0571 mole) of 3-isopropenyl-α,α-dimethylbenzyl isocyanate and 42 μl of a xylene solution containing 3% by weight of platinum complex of 1,3-divinyl-1,1,3,3-tetramethyldisiloxane. The mixture was stirred at 50° C. for 6 hours and then subjected to vacuum distillation at 150° C./3 mmHg to remove the low-boiling components, whereby 21.7 g of a product was obtained. The product was measured for IR absorption spectrum and 1H-NMR spectrum. The results were as follows.

Figure 3:
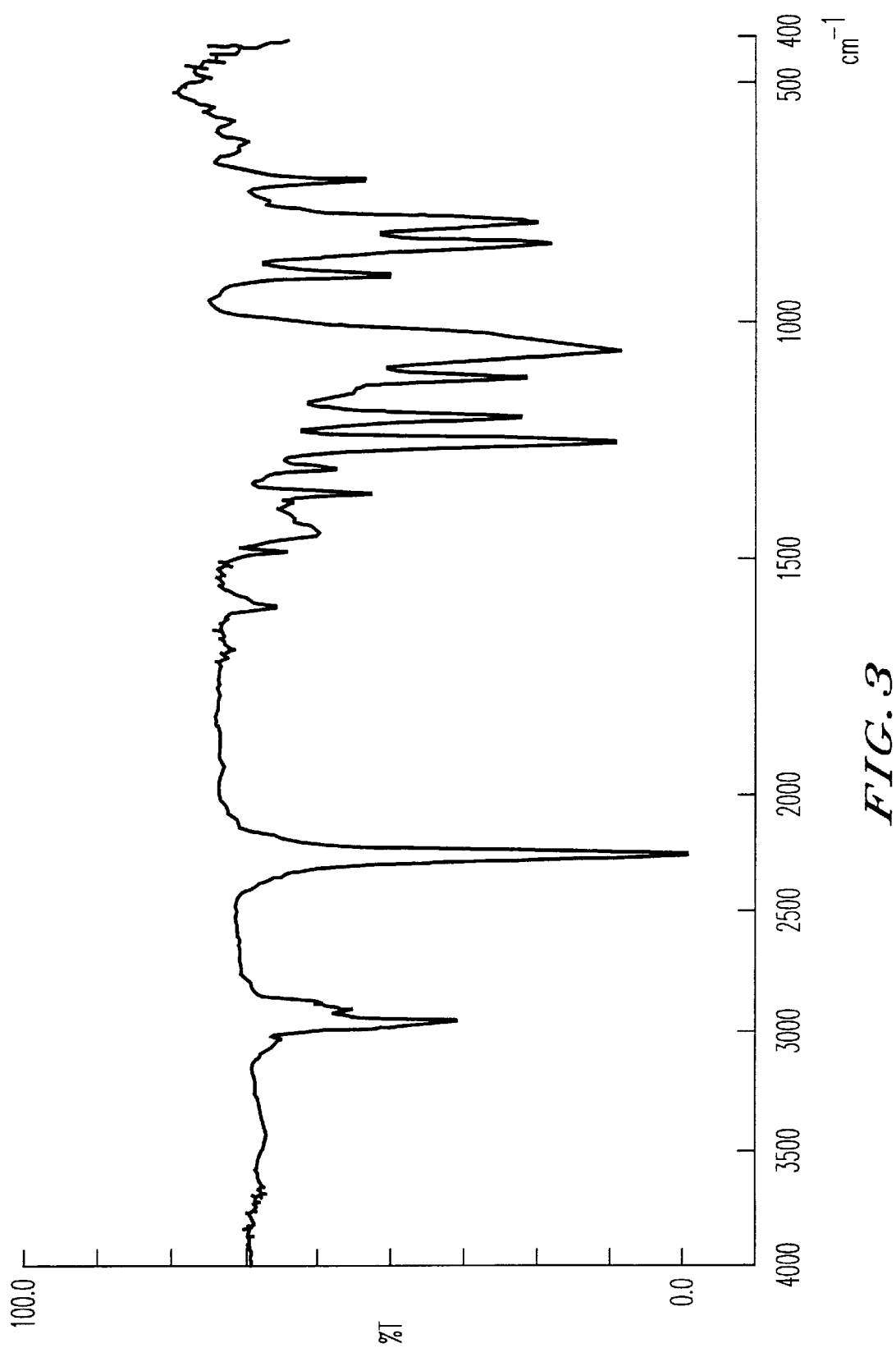
FIG. 3 is an infrared absorption spectrum of the compound obtained in Example 3.
Figure 4:
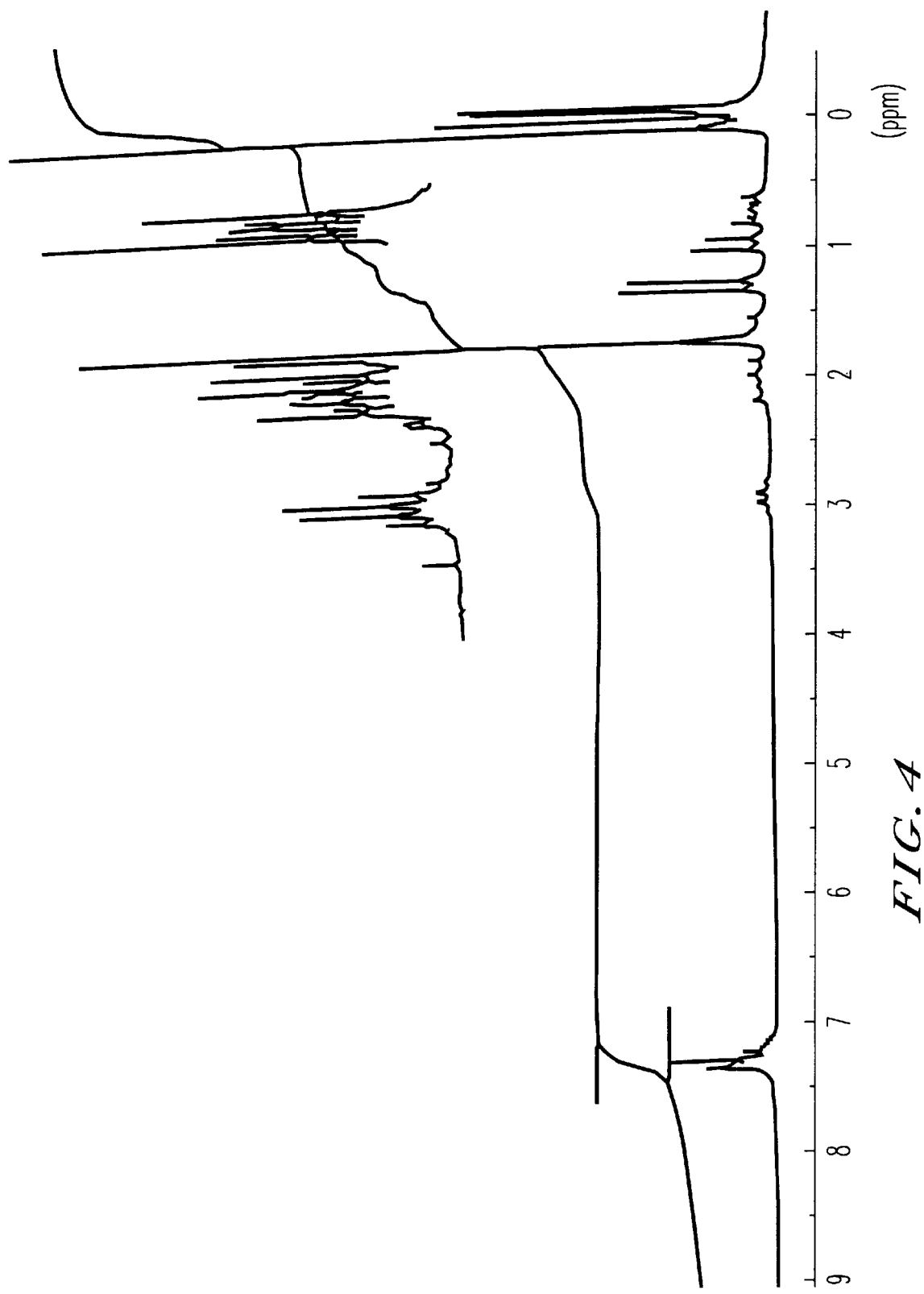
FIG. 4 is a 1H-NMR spectrum of the compound obtained in Example 3.

IR absorption spectrum: shown in FIG. 3. 1H-NMR spectrum: shown in FIG. 4.

From the above results, the substance obtained was confirmed to be an isocyanate group-containing disiloxane represented by the following structural formula (18). Yield=97%

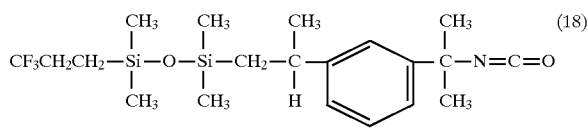

Example 4
Production of Fluorine-containing Siloxane

Into a 500-ml four-necked flask equipped with a stirrer and a dropping funnel were fed 21.1 g (0.209 mole) of triethylamine, 25.0 g (1.39 mole) of pure water and 100 g of tetrahydrofuran. Thereto was dropwise added 75.0 g (0.139 mole) of (heptadecafluoro-1,1,2,2-tetrahydrodecyl)dimethylchlorosilane with ice-cooling. After the completion of the dropwise addition, the mixture was stirred for 1.5 hours while the mixture was kept at 10° or lower. GC analysis of the reaction mixture showed that the chlorosilane was completely hydrolyzed. An aqueous acetic acid solution was added to make the mixture acidic. Thereto was added 180 g of hexane to extract an intended silanol. The extract was washed with a saturated aqueous sodium hydrogencarbonate solution and pure water in this order and then dried on anhydrous magnesium sulfate.

The dried extract obtained above was subjected to solvent removal by the use of an evaporator. The residue was subjected to vacuum distillation at 84.5° to 87.5° C. at 2 mmHg to obtain 44.3 g of a pure solid of (heptadecafluoro-1,1,2,2-tetrahydrodecyl)dimethylsilanol. Yield=61%.

42.0 g (0.0804 mole) of the silanol obtained above was dissolved in 100 g of tetrahydrofuran. The solution was fed into a 300-ml four-necked flask equipped with a stirrer, in a nitrogen atmosphere. Thereto was dropwise added 52.2 ml of a hexane solution containing 1.54 moles/liter of butyllithium, with ice-cooling while care was taken not to invite temperature increase. Then, stirring was conducted for 1 hour to convert the silanol into a corresponding lithium silanolate.

A solution containing 450 g (2.25 moles) of hexamethylcyclotrisiloxane in 400 g of a tetrahydrofuran was fed into a 2,000-ml four-necked flask equipped with a stirrer, and kept at 20° C. on a water bath. Thereto was added the total amount of the above-obtained lithium silanolate solution in a nitrogen atmosphere, and living polymerization was started.

After 3 hours from the start of the living polymerization, 80% of hexamethylcyclotrisiloxane was consumed. At that timing, 15.2 g (0.161 mole) of dimethylchlorosilane and 16.3 g ((0.161 mole) of triethylamine were added; stirring was conducted overnight; then, polymerization was terminated. The resulting reaction mixture was washed with an aqueous acetic acid solution, a saturated aqueous sodium hydrogencarbonate solution and pure water in this order, and then dried on anhydrous magnesium sulfate. The dried reaction mixture was subjected to vacuum distillation at 130° C./2 mmHg to remove the low-boiling components, whereby was obtained 399 g of a fluorine-containing siloxane compound having a hydrosilyl group, represented by the following formula (19). In the formula (19), s is an integer of presumably about 80 to 90.

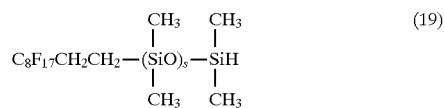

Production of Isocyanate Group-containing Siloxane

Figure 5:
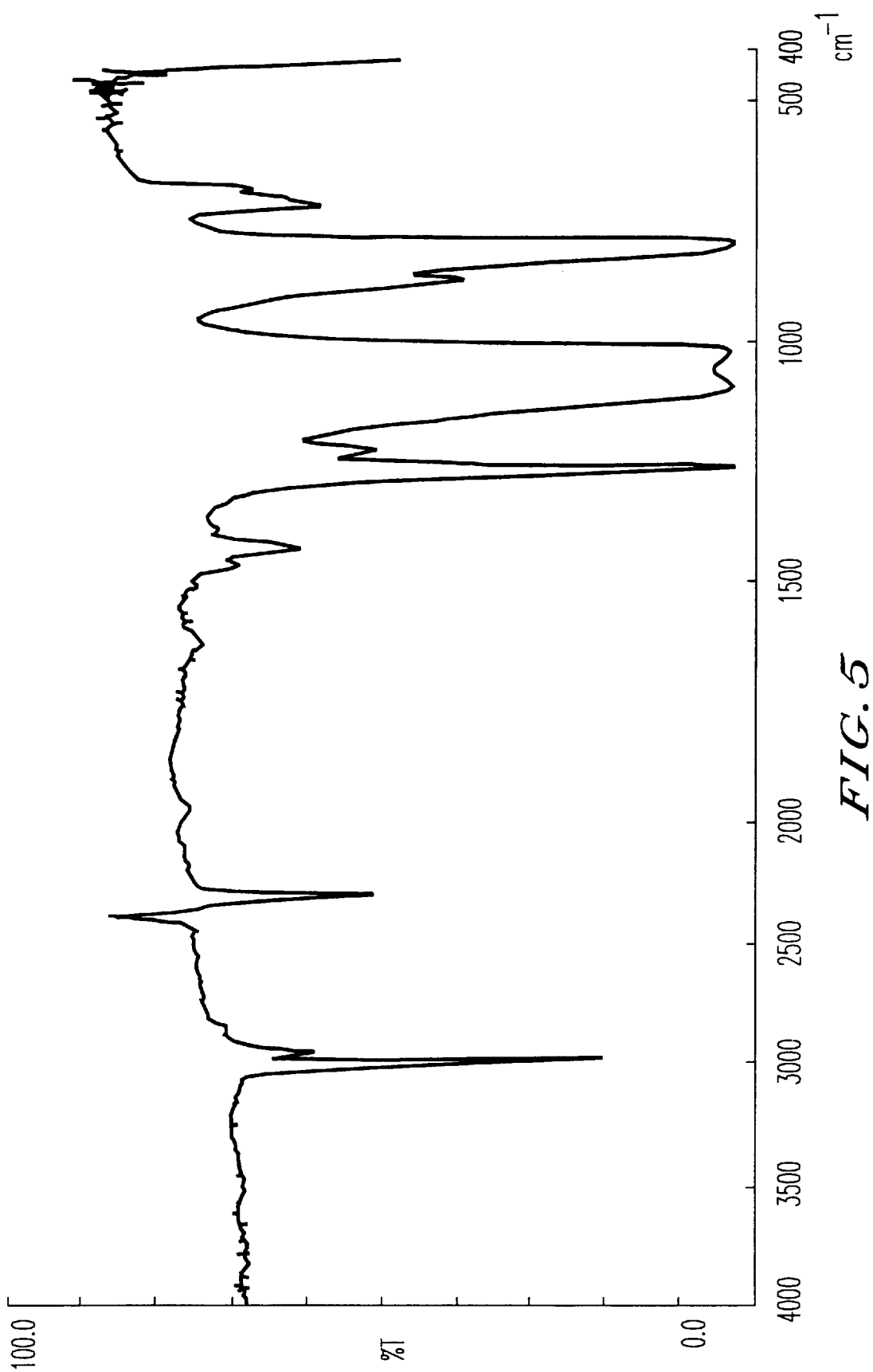
FIG. 5 is an infrared absorption spectrum of the isocyanate group-containing siloxane compound obtained in Example 4.

Into a 100-ml three-necked flask equipped with a cooler and a stirrer were fed 30.0 g of the above-obtained fluorine-containing siloxane compound having a hydrosilyl group and 1.33 g (0.0066 mole) of 3-isopropenyl-α,α-dimethylbenzyl isocyanate. The mixture was heated to 70° C. Thereto was added 42 μl of a xylene solution containing 3% by weight of platinum complex of 1,3-divinyl-1,1,3,3-tetramethyldisiloxane, and the mixture was stirred at 70° C. for 6 hours. The resulting reaction mixture was measured for IR absorption spectrum, whereby the disappearance of Si—H group was confirmed. Then, the reaction mixture was subjected to vacuum distillation at 150° C./3 mmHg to remove the low-boiling components, whereby 31.0 g of a product was obtained. The product was measured for IR absorption spectrum. The IR absorption spectrum obtained is shown in FIG. 5.

From the above results, the substance obtained was confirmed to be an isocyanate group-containing siloxane represented by the following formula (20). Yield=100%

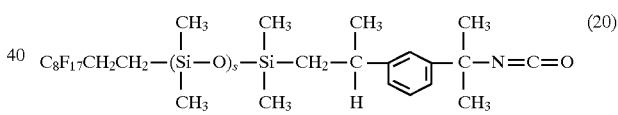

What is claimed is:
1. A process for producing a fluorine-containing siloxane compound represented by the formula (3):

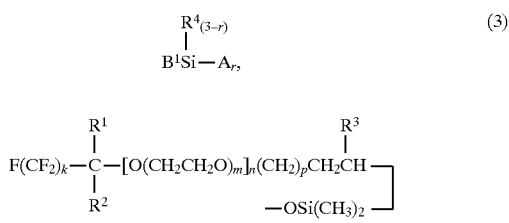

which process comprises reacting a fluorine-containing silane represented by the formula (1):

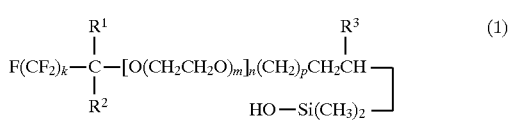

(wherein $R^1$, $R^2$, $R^3$, k, m, n and p have the same definitions as given above) with a chlorosilane represented by the formula (2):

(wherein $R^4$, $B^1$ and r have the same definitions as given above).

2. A process according to claim 1, wherein the fluorine-containing silane represented by the formula (1) is produced by hydrolyzing a fluorine-containing chlorosilane represented by the formula (5):

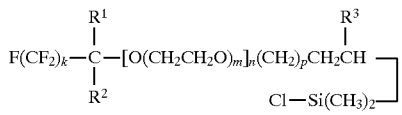

(wherein $R^1$ and $R^2$ are each independently a fluorine atom or a trifluoromethyl group, $R^3$ is a hydrogen atom or a straight chain or branched chain hydrocarbon group having 1 to 8 carbon atoms, k is an of 0 to 16, m is an integer of 0 to 30, n is 0 or 1, and p is an integer of 0 to 9).

3. A process according to claim 1 or 2, wherein $R^4$ is a methyl group.

4. A fluorine-containing siloxane compound represented by the formula (6):

wherein A is a fluorine-containing organic group represented by the formula (7):

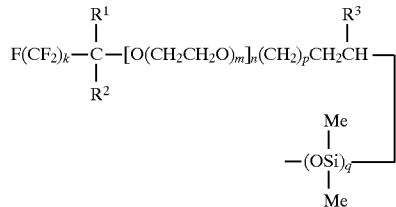

(wherein $R^1$ and $R^2$ are each independently a fluorine atom or a trifluoromethyl group, $R^3$ is a hydrogen atom or a straight chain or branched chain hydrocarbon group having 1 to 8 carbon atoms, Me is a methyl group, k is an integer of 0 to 16, m is an integer of 0 to 30, n is 0 or 1, p is an integer of 0 to 9, and q is an integer of 1 to 1,000); r is an integer of 1 to 3; $R^4$ is a monovalent hydrocarbon group having 1 to 6 carbon atoms; and $B^2$ is an isocyanate-containing group represented by the formula (8):

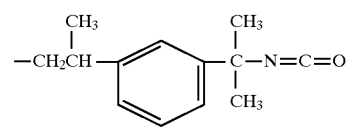

5. A process for producing a fluorine-containing siloxane compound represented by the formula (6):

[wherein A is a fluorine-containing organic group represented by the formula (7):

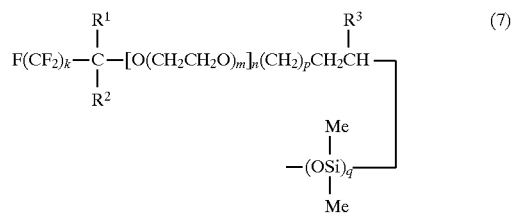

(wherein $R^1$ and $R^2$ are each independently a fluorine atom or a trifluoromethyl group, $R^3$ is a hydrogen atom or a straight chain or branched chain hydrocarbon group having 1 to 8 carbon atoms, Me is a methyl group, k is an integer of 0 to 16, m is an integer of 0 to 30, n is 0 or 1, p is an integer of 0 to 9, and q is an integer of 1 to 1,000); r is an integer of 1 to 3; $B^2$ is an isocyanate-containing group represented by the formula (8):

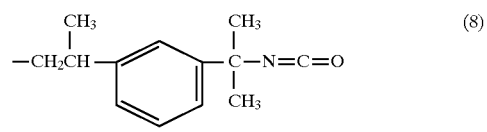

and $R^4$ is a monovalent hydrocarbon group having 1 to 6 carbon atoms], which process comprises reacting a hydrosilyl group-containing siloxane compound represented by the formula (9):

(wherein A, r and $R^4$ have the same definitions as given above) with an unsaturated group-containing isocyanate compound represented by the formula (10):

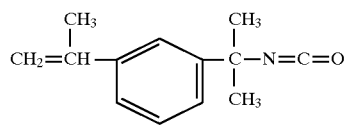

in the presence of a platinum-containing compound.

* * * * *